(12) United States Patent
Azuma et al.

(10) Patent No.: US 9,127,322 B2
(45) Date of Patent: Sep. 8, 2015

(54) YEAST HAVING IMMUNOPOTENTIATING CAPABILITY AND FOOD OR FEED

(75) Inventors: Masayuki Azuma, Osaka (JP); Taro Tachibana, Osaka (JP); Shuhei Furukawa, Itabashi-ku (JP); Ryoichi Nakajima, Itabashi-ku (JP); Hajime Watanabe, Itabashi-ku (JP); Sayumi Kobayashi, Itabashi-ku (JP)

(73) Assignees: ORIENTAL YEAST CO., LTD., Tokyo (JP); Masayuki Azuma, Osaka (JP)

( * ) Notice: Subject to any disclaimer, the term of this patent is extended or adjusted under 35 U.S.C. 154(b) by 799 days.

(21) Appl. No.: 12/797,014

(22) Filed: Jun. 9, 2010

(65) Prior Publication Data

US 2010/0310721 A1 Dec. 9, 2010

Related U.S. Application Data

(63) Continuation of application No. PCT/JP2008/072404, filed on Dec. 10, 2008.

(30) Foreign Application Priority Data

Dec. 10, 2007 (JP) ................................. 2007-318216

(51) Int. Cl.
| | |
|---|---|
| C12N 1/18 | (2006.01) |
| C12R 1/865 | (2006.01) |
| A21D 8/04 | (2006.01) |
| A23K 1/00 | (2006.01) |
| A23K 1/18 | (2006.01) |

(52) U.S. Cl.
CPC ................ *C12R 1/865* (2013.01); *A21D 8/047* (2013.01); *A23K 1/009* (2013.01); *A23K 1/1846* (2013.01); *A23K 1/1853* (2013.01); *C12N 1/18* (2013.01)

(58) Field of Classification Search
None
See application file for complete search history.

(56) References Cited

U.S. PATENT DOCUMENTS 3,889,006 A * 6/1975 Nagasawa et al. ............ 426/656

FOREIGN PATENT DOCUMENTS

| JP | 05-178759 | 7/1993 |
|---|---|---|
| JP | 06-056678 | 3/1994 |
| JP | 06-056685 | 3/1994 |
| JP | 06-271470 | 9/1994 |
| JP | 07-228536 | 8/1995 |
| JP | 2529605 | 6/1996 |
| JP | 09-266792 | 10/1997 |
| JP | 2873434 | 1/1999 |
| JP | 11-049696 | 2/1999 |
| JP | 11-092389 | 4/1999 |
| JP | 2000-281571 | 10/2000 |
| JP | 2001-181303 | 7/2001 |
| JP | 2001-354570 | 12/2001 |
| JP | 2002-003395 | 1/2002 |
| JP | 2003-081839 | 3/2003 |
| JP | 2003-128589 | 5/2003 |
| JP | 2003-183176 | 7/2003 |
| JP | 2006-075039 | 3/2006 |
| WO | 2006/025295 | 3/2006 |

OTHER PUBLICATIONS

McMurrough et al., Biochem. J. (1967) vol. 106, pp. 189-203.*
Farkas et al., Folia microbiol. Vol., pp. 21. 459-464 (1976).*
Hamada et al., Eur J. Biochem. vol. 119, pp. 365-371 (1981).*
Sakai et al., "*Saccharaomyces cerevisiae* Mutant Displaying β-Glucans on Cell Surface," Journal of Bioscience and Bioengineering, vol. 103, No. 2, p. 161-166 (2007).
Maneesri et al., "Deletion of MDC4 Involved in Glycosylphosphatidylinositol (GPI) Anchor Synthesis Leads to an Increase in β-1,6-Glucan Level and a Decrease in GPI-Anchored Protein and Mannan Levels in the Cell Wall of *Saccharaomyces cerevisiae*," Journal of Bioscience and Bioengineering, vol. 99, No. 4, p. 354-360 (2005).
International Search Report for application No. PCT/JP2008/072404, dated Feb. 3, 2009 (4 pages).
Sung et al., "Yeast mannans inhibit binding and phagocytosis of zymosan by mouse peritoneal macrophages," The Journal of Cell Biology, 1983, vol. 96, pp. 160-166.
Shimokawa et al.,"Isolation of a *candida albicans* mutant with reduced content of cell wall mannan and deficient mannan phosphotylation," Sabouraudia, 1984, vol. 22, No. 4, pp. 315-321.

* cited by examiner

*Primary Examiner* — Irene Marx
(74) *Attorney, Agent, or Firm* — Hamre, Schumann, Mueller & Larson, P.C.

(57) ABSTRACT

A yeast including a cell wall having a low mannan content, wherein the yeast has an immunopotentiating capability, and is able to grow in a YPD liquid medium with an osmotic pressure of 300 mOsm, and wherein, when a part of a pre-culture of the yeast grown in a YPDS liquid medium is added to the YPD liquid medium so that $OD_{660}$ is adjusted to 0.1, followed by incubating at 30° C. for 24 hours, the yeast grows to increase the $OD_{660}$ of the YPD liquid medium to 1.0 or more.

2 Claims, 3 Drawing Sheets

FIG. 1

Bar = 10 μm

YEAST HAVING IMMUNOPOTENTIATING CAPABILITY AND FOOD OR FEED

CROSS-REFERENCE TO RELATED APPLICATION

This is a continuation application of PCT/JP2008/072404, filed on Dec. 10, 2008.

TECHNICAL FIELD

The present invention relates to a yeast which is highly safe and is able to exert a high immunopotentiating capability even when taken as whole cell, as well as a food or feed that contains the yeast.

BACKGROUND ART

An immune system is a system by which a body protects itself from attacks by foreign viruses and bacteria, as well as cancer cells. Although many types of cells are involved in the immune system, the important roles the macrophage plays in the system is recognized. Macrophage is ubiquitously found in all animals, and is involved in all steps of immune response, including the primary step.

It is known that various types of diseases, such as cancer, infections, and allergies, are triggered when the immune system is compromised. Conversely, if the immune system is stimulated, there is great hope for various positive effects such as oncogenic suppression, anticancer effect, anti-infection, and anti-allergy, as well as recovery of biorhythms and maintenance of homeostasis.

Thus, many researchers provide various compounds and microbes that have immunopotentiating effects, in order to improve consumers' health condition. Examples of the compounds and microbes include those containing lactoferrin hydrolysate (see, for example, Japanese Patent Application Laid-Open (JP-A) No. 05-178759), sugars such as chitin (see, for example, JP-A No. 06-271470), trehalose (see, for example, JP-A No. 2003-81839), fucoidan (see, for example, JP-A No. 2001-181303), plant derivatives (see, for example, JP-A No. 06-56685), peptides (see, for example, Japanese Patent (JP-B) No. 2873434), interleukins (see, for example, JP-A No. 2002-3395), nucleic acids (see, for example, JP-B No. 2529605), glutathione (see, for example, JP-A No. 11-49696), amino acids (see, for example, JP-A No. 2000-281571), polylysin (see, for example, JP-A No. 2003-128589), and microbes such as enteric bacteria (see, for example, JP-A No. 06-56678), lactic acid bacteria (see, for example, JP-A No. 07-228536) and *enterococcus* bacteria (see, for example, JP-A No. 11-92389).

Also recently, the immunopotentiating effects of β-glucan have attracted much attention, and some have suggested methods of immunopotentiation using β-glucan which is purified from yeasts or mushrooms (see, for example, JP-A Nos. 2001-354570 and 2003-183176).

However, in order to potentiate consumers' immunity using these immunopotentiating compounds, a large amount of these compounds must be purified and given to the consumers, which involves many manufacturing processes as well as much cost and labor. In addition, properties of some of these immunopotentiating microbes are unknown and not suitable for consumption. Some of these immunopotentiating microbes must be added to food separately, if they cannot be used directly for the manufacturing processes (e.g., fermentation).

Some Patent Literatures disclose yeasts having an immunopotentiating capability, which are obtained by knocking out one or more genes selected from the group consisting of MCD4, GAS1 and CWH41 belonging to the genes on the yeast chromosome (see, for example, JP-A No. 2006-75039). The yeast disclosed in the JP-A No. 2006-75039 is able to exert an immunopotentiating effect, even when the yeast is given as whole cell and without purifying β-glucan from it as described in JP-A Nos. 2001-354570 and 2003-183176.

However, in the yeast disclosed in JP-A No. 2006-75039, the specific genes mentioned above are knocked out by recombinant DNA technologies. In recent years, with the development of recombinant DNA technologies, numerous genetically modified foods have been approved and commercialized after their safety was confirmed. The anxieties over the safety of such genetically modified foods are still considerable among consumers. Therefore, using the yeast disclosed in JP-A No. 2006-75039 in foods is commercially difficult at this moment.

Furthermore, the yeast disclosed in JP-A No. 2006-75039 exhibits a very low growth rate in media with a low osmotic pressure, as it might be expected from the fact that the yeast is lack of the genes involved in the structure of its cell wall. Thus, the incubation of the yeast poses problems such as high cost. Specifically, in order not to put pressure on the structurally fragile cell wall, sugar or other ingredients must be added to its growth media to increase the osmotic pressure so that the media has the same osmotic pressure as the intracellular liquid. In addition, if the yeast is used for fermentation of foods such as bread, there are other problems such as constricted fermentation conditions or changed food flavor due to the sugar added to make an isotonic fermentation solution.

On the other hand, mutagenesis induces mutation in DNA using mutagens, such as mutagenic compounds, UV irradiation, or radiation. And, mutagenesis induces mutation at a rate higher than that found in nature. The mutagenesis does not introduce any foreign DNA sequences (i.e., DNA sequences other than the sequences an organism naturally has), in contrast to the above described recombinant DNA methods. Thus, consumers accept foods whose genetic properties have been changed through mutagenesis as something relatively safe.

As described above, there have been no microbe such as a yeast that is highly safe, able to exert an immunopotentiating effect when taken as whole cell, easily obtained and inexpensive, usable for manufacturing of food without any particular pre-treatments, and amenable to incubation under low osmotic pressures. Therefore, keen demand has arisen for such microbes.

DISCLOSURE OF INVENTION

The present invention aims to solve the above-described problems and to achieve the following purposes. Specifically, the present invention aims to provide a yeast that is highly safe, is able to exert an immunopotentiating effect even when taken as whole cell, is easily obtained and inexpensive, is usable for manufacturing of food without any particular pre-treatments, and amenable to incubation under low osmotic pressures. The present invention also aims to provide a food or feed which contains the yeast described above.

The inventors of the present invention conducted intensive studies in order to solve the above-described problems, and have obtained the following findings. Specifically, a mutant yeast whose cell wall has a low mannan content was obtained when ethyl methanesulfonate-induced mutagenesis introduced mutation into the chromosomal DNA of a yeast widely used in food manufacturing. The β-glucan in the cell wall is exposed on the cell surface due to its low mannan content; thus, the yeast exhibited a significant immunopotentiating capability even when the whole cell (i.e., without purifying β-glucan from cells) was used in immunopotentiation tests. The yeast unexpectedly showed high tolerance to hypotonic pressure, proving that it can be efficiently manufactured (incubated) and that a food or feed containing it can be suitably manufactured.

The present invention is accomplished on the basis of the findings described above. Means for solving the above existing problems are as follows.

<1> A yeast including:
  a cell wall having a low mannan content,
  wherein the yeast has an immunopotentiating capability, and is able to grow in a YPD liquid medium with an osmotic pressure of 300 mOsm, and wherein, when a part of a pre-culture of the yeast grown in a YPDS liquid medium is added to the YPD liquid medium so that $OD_{660}$ is adjusted to 0.1, followed by incubating at 30° C. for 24 hours, the yeast grows to increase the $OD_{660}$ of the YPD liquid medium to 1.0 or more.
<2> The yeast according to <1> above, wherein the immunopotentiating capability is a macrophage activating capability.
<3> The yeast according to one of <1> and <2> above, wherein the yeast acquires the immunopotentiating capability through mutagenesis.
<4> The yeast according to any one of <1> to <3> above, wherein the yeast is not recombinantly modified.
<5> The yeast according to one of <3> and <4> above, wherein a parent strain used for the mutagenesis is *Saccharomyces cerevisiae*.
<6> The yeast according to any one of <3> to <5> above, wherein the mutagenesis is induced by any one of a mutagenic compound, UV irradiation and radiation.
<7> The yeast according to any one of <1> to <6> above, wherein the yeast is one of *Saccharomyces cerevisiae* FERM BP-11293 and *Saccharomyces cerevisiae* FERM BP-11294.
<8> A food or feed including:
  the yeast according to any one of <1> to <7> above.

The present invention can solve the existing problems pertinent in the art by providing a yeast that is highly safe, is able to exert an immunopotentiating effect even when taken as whole cell, easily obtainable, inexpensive, usable for manufacturing of food without any particular pre-treatment, and amenable to incubation under low osmotic pressures. Furthermore, the present invention can provide a food or feed that contains the yeast described above.

BEST MODE FOR CARRYING OUT THE INVENTION

<Yeast>

The yeast of the present invention has a cell was with a low mannan content, an immunopotentiating capability, and the ability to grow in a YPD liquid medium having an osmotic pressure of 300 mOsm.

<Immunopotentiating Capability>

The immunopotentiating capability is an ability to potentiate innate immunity. Innate immunity is a part of the immunity living organisms innately have, and expels any antigen even if the living organisms are not exposed thereto. These antigens are not especially limited, and they may include any external antigens such as viruses or bacteria, or internal antigens such as cancer cells.

The immunopotentiating capability is not especially limited, as long as it can potentiate innate immunity. The immunopotentiating capability may include activation of any immune cells according to the intended purpose. The immune cells may be phagocytes (macrophage, monocyte, neutrophil and dendritic cell), antigen-presenting cells (macrophage and dendritic cell), natural killer (NK) cells, polymorphonuclear leukocytes (acidophilic leukocyte, basophilic leukocyte and mastcyte). The capability to activate macrophages is especially preferable, as macrophages ubiquitously exist among various organisms, and activation of macrophages is highly effective in the removal of antigens.

The evaluation method used to evaluate the immunopotentiating capability of the yeast is not especially limited. It may be appropriately selected from any conventionally known evaluation methods according to the type of the cells involved in innate immunity.

For example, the macrophage activation capability can be evaluated by measuring the amount of cytokine produced by macrophages (e.g., TNF-α) before and after macrophage stimulation, which is induced by allowing macrophages to come into contact with the yeast in media or buffer solutions.

One possible reason why the yeast has an immunopotentiating capability is that its β-glucan, which has an immunopotentiating capability, is exposed on the cell surface since the cell wall has a low mannan content.

<Mannan>

Mannan is generally one of the main constituent components of the yeast cell wall, and is an oligosaccharide chain composed mainly of D-mannose. Mannan is bound to a protein and exists as a mannan-protein. In the yeast cell wall, a layer of β-glucan is laid along the outer surface of the cell membrane, and the mannan-protein is bound to the β-glucan via a glycolipid called GPI (glycosylphosphatidylinositol) anchor. As a result, mannan is placed in the outermost layer of the cell wall (i.e., the cell surface) so as to cover the β-glucan. In contrast, the yeast of the present invention has β-glucan, instead of mannan, exposed on its cell surface as its cell wall contains less mannan.

Though the reason why the cell wall of the yeast contains less mannan is unclear, the following reasons may be possible causes of this condition. Specifically, mannan, mannan-protein and/or GPI anchor is not synthesized, synthesized mannan, synthesized mannan-protein, and/or synthesized GPI anchor is not transported across the cell membrane, or their binding sites are either lost or modified.

The low mannan content of the cell wall of the yeast can be confirmed with mannan-specific antibodies, lectins or the like, such as ConA (Concanavalin A) lectin that binds specifically to, for example, D-mannose and methyl-α-D-mannopyranoside contained in mannan. Specifically, antibodies and/or ConA is labeled with a fluorescent dye, such as FITC (Fluorescein isothiciante), in order to detect their binding to the cell surface based on fluorescence. In this case, if any cell-surface fluorescence attributed to the binding of these antibodies or CanA is not detected, the cell wall is deemed as containing less mannan. The detection of the fluorescence may be performed either visually under a fluorescent microscope, or quantitatively with a flow cytometer or a fluorescence plate reader.

The low mannan content of the cell wall of the yeast may be determined by quantifying the mannan content of the cell wall. The method of quantifying the mannan content is not especially limited, but, for example, may be performed according to the protocol described below.

Specifically, first, cells are disrupted with glass beads, and a cell wall fraction is prepared by ultracentrifugation, followed by freeze-drying. Then, the fraction is hydrolyzed with sulfuric acid following the method described by Dallies et al. (Yeast 14 (1998), pp. 1297-1306). After neutralization, the supernatant is freeze-dried, and analyzed through HPLC using a column such as REZEX™ RPM-Monosaccharide Phenomenex (Shimadzu GLC LTD). The mannan content of the cell wall can be determined by calculating the ratio between glucose and mannose.

The mannan content of the cell wall is not especially limited, so long as it is reduced to such an extent that allows β-glucan to be exposed on the cell surface. It is more preferable that the cell wall contains no mannan.

β-Glucan is one of the main constituent components of the yeast cell wall, and an oligosaccharide chain formed by β1-3 type binding of glucose.

The average molecular weight or the manner of modification of β-glucan is not especially limited, so long as it possesses immunopotentiating capability, and may change according to the type of yeast or the incubation conditions.

The method of confirming that β-glucan is exposed on the cell surface is not especially limited, but any method may be appropriately selected according to the intended purpose. For instance, whether or not β-glucan is exposed on the cell surface may be confirmed by using β-glucan-specific antibodies or fluorescent reagents such as aniline blue. Alternatively, the exposed β-glucan on the cell surface may be confirmed by observing β-glucan filaments on the cell surface under an electron microscope.

<Tolerance to Hypotonic Pressure>

In general, cell walls of microbes (including yeast) and plants have very important functions such as tolerance to hypotonic pressure, and maintaining cell morphology.

There was concern that the yeast of the present invention might have lost the tolerance to hypotonic pressure, as its cell wall contains a low mannan content. However, unexpectedly, the yeast produced by the present inventors has tolerance to hypotonic pressure, as described in Examples described below.

The indicator of the tolerance of the yeast to hypotonic pressure is not especially limited, so long as it does not impair the effects of the present invention, and may be appropriately selected from any indicators according to the intended purpose. It is preferred that the yeast can grow in a YPD liquid medium having an osmotic pressure of 300 mOsm. The YPD liquid medium contains 1% by mass yeast extract, 2% by mass peptone and 2% by mass glucose. Furthermore, the yeast extract, peptone and glucose, contained in the YPD liquid medium, are obtained respectively from Oriental Yeast Co. Ltd, Nihon Pharmaceutical Co. Ltd. and Kokusan Chemical Co. Ltd.

The osmotic pressure may be adjusted by non-fermenting sugars such as sorbitol, NaCl, or the like.

The osmotic pressure may be determined by, for example, an osmometer F-2000 (product of Roebling).

As used herein, the phrase "able to grow" means that, when a part of a pre-culture of the yeast grown in a YPDS liquid medium (a hypertonic medium) is added to the aforementioned YPD liquid medium so that $OD_{660}$ is adjusted to 0.1, followed by incubating with shaking under appropriate conditions for 24 hours, the yeast grows to increase the $OD_{660}$ of the YPD liquid medium to 1.0 or more. Here, the YPDS liquid medium is composed of 1% by mass yeast extract, 2% by mass peptone, 2% by mass glucose and 5.5% by mass (0.3 mol/L) sorbitol. Notably, the yeast extract, peptone, glucose and sorbitol, contained in the YPDS liquid medium, are obtained respectively from Oriental Yeast Co. Ltd, Nihon Pharmaceutical Co. Ltd., Kokusan Chemical Co. Ltd, and Wako Pure Chemical Industries Ltd.

If the yeast subjected to a growth test requires uracil, the YPD and YPDS liquid media used during the test should be supplemented with uracil in an amount of 0.3% by mass or more with respect to the glucose content. In other words, the uracil content of the YPD or YPDS liquid medium is $6 \times 10^{-3}$% by mass or more, if they contain 2% by mass glucose.

If the yeast subjected to the growth test has any other growth requirements, the YPD and YPDS liquid media used in the test should be supplemented with an adequate amount of required substances.

The $OD_{660}$ of these media may be measured using a spectrophotometer. Since the above yeast can grow in the YPD medium having an osmotic pressure of 300 mOsm, a growth medium therefor does not require a supplement to increase the osmotic pressure, leading to reduction of incubation cost. In addition, if the yeast is added to foods, the manufacturing efficiency of the foods may be improved due to an increase in living cell recovery rate, for the yeast cells would not lyse even when they are washed with a hypotonic solution.

The type of the yeast is not especially limited, and may be appropriately selected according to the intended purpose. Examples thereof include bread yeasts, beer yeasts, wine yeasts, sake yeasts and miso/soy-sauce yeasts, with bread yeasts being preferable.

The family of the yeast is not especially limited, and may be appropriately selected according to the intended purpose. Examples thereof include Saccharomyces family, Zygosaccharomyces family, Yarrowia family, Williopsis family, Torulaspora family, Candida family, Rhodotorula family and Pichia family.

Examples of species of the yeast include *Saccharomyces cerevisiae, Saccharomyces pastorianus, Saccharomyces bayanus, Zygosaccharomyces Candida saitoana, Candida tropicalis, Yarrowia lipolytica, Torulaspora delbrueckii, Candida sake, Candida tropicalis, Candida utilis, Pichia anomala, Williopsis saturnus, Saccharomycopsis fibligera, Rhodotorula glutinis* and *Pichia farinosa*.

Among them, *Saccharomyces cerevisiae* and *Saccharomyces pastorianus* are more preferred, with *Saccharomyces cerevisiae* being particulalry preferred.

The *Saccharomyces cerevisiae* is not especially limited, and may be appropriately selected according to the intended purpose. Preferred examples thereof include *Saccharomyces cerevisiae*FERM BP 11291, *Saccharomyces cerevisiae* FERM BP-11292, *Saccharomyces cerevisiae*FERM BP-11293 and *Saccharomyces cerevisiae* FERM BP-11294. From the viewpoint of exhibiting a high immunopotentiating capability, *Saccharomyces cerevisiae* FERM BP-11293 and *Saccharomyces cerevisiae* FERM BP-11294 are particularly preferred.

*Saccharomyces cerevisiae* FERM BP 11291, *Saccharomyces cerevisiae* FERM BP-11292, *Saccharomyces cerevisiae* FERM BP-11293 and *Saccharomyces cerevisiae* FERM BP-11294 are yeasts created by the present inventors, and deposited to International Patent Organism Depository at National Institute of Advanced Industrial Science and Technology of Japan.

Although chromosomal mutation sites of *Saccharomyces cerevisiae* FERM BP 11291, *Saccharomyces cerevisiae* FERM BP-11292, *Saccharomyces cerevisiae* FERM BP-11293 and *Saccharomyces cerevisiae* FERM BP-11294 have not been precisely identified yet, it has been found that *Saccharomyces cerevisiae* FERM BP-11294 carries mutation on a (app.) 10,000-bp-fragment of the BamHI-digested chromosome 15. The fragment contains complete RPS12, MRS6, GPB1, RAD17, and NDD1 genes as well as a part of SCP 1 gene. This suggests that the immunopotentiating capability of *Saccharomyces cerevisiae* FERM BP-11294 is not caused by the mutations disclosed in JP-A No. 2006-75039, which are located in MCD4, GAS1, and CWH41 genes.

The genome number of the yeasts (i.e., ploidy, such as haploid) is not especially limited and may be appropriately selected according to the intended purpose.

—Incubation Protocol—

The incubation protocol for the yeast is not especially limited, and may be appropriately selected from any protocols well known in the art according to the intended purpose. For instance, batch incubation or flow incubation, or the like, may be employed.

A jar fermentor may be suitably used for the incubation. The jar fermentor settings are not especially limited and may be appropriately selected. For example, the incubation temperature may range from about 28° C. to about 33° C., the incubation time from about 1 hour to about 120 hours, the pH from about 4 to about 7, the aeration from about 0 vvm to about 5 vvm, and the stirring speed from about 100 rpm to about 700 rpm.

—Use—

The use of the yeast is not especially limited and may be appropriately selected according to the specific purpose. Uses as food ingredients to be added to foods, or as feeds is preferred, with the use as food ingredients being particularly preferred. The yeast may be suitably used for manufacturing of foods/beverages, such as fermentation in bread or beer making. The food or feed having an immunopotentiating capability may be manufactured using the yeast of the present invention. The yeast may be used in the following states: with/without cell disruption, dried, non-dried and/or live.

The method of the cell disruption is not especially limited and may be appropriately selected according to the intended purpose. Physical cell disruption using, for example, a dyno mill, or chemical cell disruption may be used.

The subject to which the yeast is applied is not especially limited, so long as it has innate immunity. It may be human or non-human animals. Examples of the non-human animals include domestic animals (e.g., horse, cattle, swine, sheep, goat, camel and lama), laboratory animals (e.g., mouse, rat, guinea pig and rabbit), poultry (e.g., chicken, duck, turkey and ostrich), fish (e.g., red sea bream, striped knifejaw, flatfish, yellowtail, gold-striped amberjack, tuna, white trevally, sweetfish, salmon/trout, pufferfish, eel, loach and catfish), crustaceans (e.g., Japanese tiger prawn, black tiger prawn, fleshy prawn and blue crab), shellfish (e.g., abalone, horned turban, scallop and oyster) and pet animals (e.g., dog and cat).

<Method for Producing Yeast>

The yeast may be produced through mutagenesis for inducing one or more mutations on the chromosomes of its parent strain, which is suitable for consumption. The strains may be identified among natural mutants (i.e., carrying naturally occurred chromosomal mutations) of the parent strains that are suitable for consumption.

The identity of the parent strain is not especially limited and may be appropriately selected according to the intended purpose. For instance, the yeasts described in the preceding <Yeast> section may be used.

Here, the mutagenesis refers to any methods that induce DNA mutations at higher frequencies than found in nature by means of mutagen, such as mutagenic agents, UV irradiation, radiation, or the like. The method enables mutations to be induced in chromosomes without involving introduction of foreign nucleic base sequences (nucleic base sequences other than those the organism naturally possesses).

The mutagenic agents are not especially limited, and may be appropriately selected according to the intended purpose. Examples thereof include ethyl methanesulfonate, nitrosoguanidine and 5-bromouracil.

The radiation may be of X-ray, α-ray, β-ray, γ-ray, particle ray or the like.

The method of screening after the mutagenesis treatment to identify mutant strains having an immunopotentiating capability is not especially limited and may be appropriately selected according to the intended purpose. For instance, viability in selection media, mannan content of cell surface layer, or macrophage activation capability may be employed as a screening indicator.

The genes targeted by the mutagenesis/natural mutation are not especially limited, so long as the caused mutations allow parent strains to acquire an immunopotentiating capability. Examples of the targeted genes include RPS12, MRS6, GPB1, RAD17, NDD1, SCP1, MCD4, GAS1 and CWH41. Alternatively, the mutations may be introduced in any other base sequences of the chromosomes.

The type of the mutations is not especially limited, so long as they allow a parent strain to acquire an immunopotentiating capability. They may be base substitution, insertion, deletion or inversion.

(Food or Feed)

A food or feed of the present invention contains the yeast described above.

The type of the food is not especially limited and may be selected according to the intended purpose from foods, such as breads, confectionaries such as biscuit or scone, hospital foods, liquid foods, processed seafood/meat, noodles, seasonings, beverages such as beer or juice, health foods, functional drinks or others.

The type of the feed is not especially limited, and any feed may be selected according to the intended subject. The subject is not especially limited, and any intended subjects mentioned as examples in the —Use— section may be used.

The food or feed exhibits a high immunopotentiating capability by virtue of the yeast they contain, which possesses a high immunopotentiating capability.

EXAMPLES

The present invention will next be described by way of examples, which should not construed as limiting the present invention thereto.

Example 1

—Production of Yeasts Having Immunopotentiating Capability—

—Mutagenic Treatment—

T-21U strain, a uracil-requiring mutant strain of T-21 (Oriental Yeast Co. Ltd., a haploid of commercial baker's yeast), was used as a parent strain to be subjected to mutagenic treatment.

The T-21U strain is a natural mutant strain selected by the following method: T-21 strain cells incubated in a YPD liquid medium were plated on a medium containing 5-fluoroorotic acid (0.7% by mass Yeast Nitrogen Base (DIFCO), 2% by mass glucose, 0.1% by mass 5-fluoroorotic acid, 0.05% by mass uracil and 2% by mass agar), and incubated for 3 days at 30° C.

The parent strain cells were incubated overnight in a uracil-supplemented YPD medium (1% by mass yeast extract (Oriental Yeast Co. Ltd.), 2% by mass peptone (Nihon Pharmaceutical Co. Ltd.), 2% by mass glucose (Kokusan Chemical Co. Ltd.), $6\times10^{-3}$% by mass uracil (Wako Pure Chemical Industries Ltd.); the suppliers of these compounds are the same throughout Examples). The thus-incubated cells were dispensed to 2 Eppendorf tubes and harvested by ultracentrifugation. After the removal of the supernatant, the cells were washed twice with sterilized water and re-suspended in 0.1 M (mol/L) phosphate buffer (pH 7.0). Ethyl methanesulfonate (EMS) (30 μL) was added to the cell suspension, followed by incubating for 1 hour at 30° C. with shaking. The cells were recovered by ultracentrifugation, and after the removal of the supernatant, they were re-suspended in 2004 of a solution containing 5% by mass sodium thiosulfate. The cell suspension was transferred to new tubes, and the cells were recovered by ultracentrifugation, followed by washing twice with 2004 of a solution containing 5% by mass sodium thiosulfate. The cells were re-suspended in 1 mL of sterilized water, and appropriately diluted before plated on a YPD agar medium.

—Screening—

The yeasts produced through the above mutagenic treatment were screened for immunopotentiating capability through 3 screening steps (from the first to the third) described below.

The first screening was performed for selecting cell-wall mutant strains. The above-prepared culture was plated on a uracil-supplemented YPD agar medium (1% by mass yeast extract, 2% by mass peptone, 2% by mass glucose, $6\times10^{-3}$% by mass uracil and 2% by mass agar), a uracil-containing 1/5YPD agar medium (0.2% by mass yeast extract, 0.4% by mass peptone, 0.4% by mass glucose, $1.2\times10^{-3}$% by mass uracil and 2% by mass agar), and a uracil-containing 1/5YPD+0.05% SDS agar medium. After 3-day incubation at 30° C., selection was performed on the strains that grew slower on the uracil-containing 1/5YPD agar medium than on the uracil-containing YPD agar medium, upon comparison between the uracil-containing YPD agar medium and the uracil-containing 1/5YPD agar medium (1) and that grew slower (or died) on the uracil-containing 1/5YPD+0.05% SDS agar medium than on the uracil-containing 1/5YPD agar medium, upon comparison between the uracil-containing 1/5YPD agar medium and the uracil-containing 1/5YPD+ 0.05% SDS agar medium (2).

In total, 3120 mutant strains were selected as a result of the first screening. For the second screening, the cells of the selected strains were mannan stained using FITC-labeled ConA. A colony was removed with a toothpick and suspended in a PBS+1.0 M sorbitol solution. The cells were recovered by ultracentrifugation and re-suspended in a PBS+1.0 M sorbitol solution. The cell suspension was mixed with FITC-labeled ConA solution (Sigma) and left to stand in the dark for 30 minutes at room temperature. After washing once, the cells were observed under a fluorescent microscope using Blue excitation light. Selection was performed on the strains that neither exhibited significant fluorescent light as a whole, nor had fluorescene confirmed on their photographic images.

Four strains out of 3120 strains were selected as a result of the second screening (Mutants 1 to 4).

Figure 1:
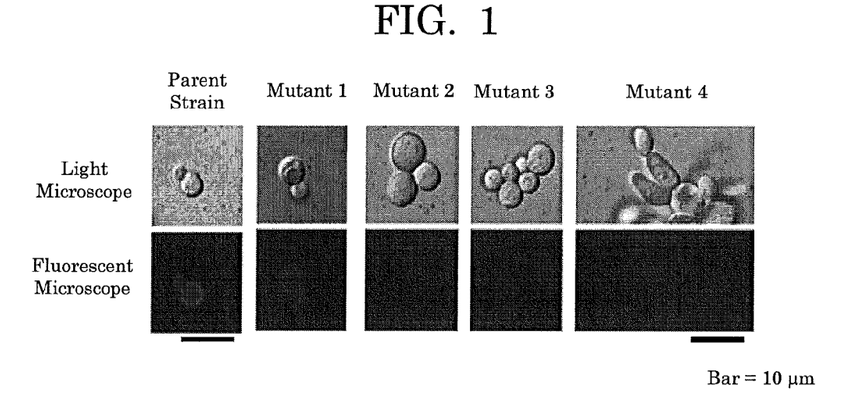
FIG. 1 is a set of microscopic images of Mutants 1 to 4.

FIG. 1 is a set of microscopic images of Mutants 1 to 4, in which the images of the upper row are those taken with a light microscope, and the images of the lower row are those taken with a florescent microscope after mannan staining. As shown in FIG. 1, almost no fluorescence is observed among Mutants 1 to 4. In particular, no fluorescence is observed among Mutants 2 to 4.

Mutant 1 is *Saccharomyces cerevisiae* FERM BP 11291, Mutant 2, *Saccharomyces cerevisiae* FERM BP-11292, Mutant 3, *Saccharomyces cerevisiae* FERM BP-11293 and Mutant 4, *Saccharomyces cerevisiae* FERM BP-11294. Each of the 4 mutants was deposited to the International Patent Organism Depository at National Institute of Advanced Industrial Science and Technology of Japan.

The third screening was performed based on the macrophage activation capability of Mutants 1 to 4. The cells of Mutants 1 to 4 were harvested through centrifugation, and treated with ethanol, followed by washing twice with sterilized water. The cells (yeasts) were washed with an RPMI-1640 medium and re-suspended in the same medium, and then were counted using a cell-counting chamber. The cell (yeast) concentration was adjusted to a specified value for preparation of samples.

Macrophages incubated for 2 days were used for the test. The macrophages were harvested from an incubation flask, washed twice with a new medium, and counted using a cell-counting chamber. The macrophage concentration was adjusted to a specified value to give a macrophage culture for activity measurement.

The macrophage culture was dispensed into a 24-well plate, and the above-prepared samples were added thereto so that the ratio of yeast cells to macrophages would become 30:1 by cell number. After 6-hour incubation at 37° C. under 5% $CO_2$, the culture was transferred to tubes and ultracentrifugated. The supernatant was collected, and the amount of TNF-α protein in the supernatant was analyzed using Quantikine Mouse TNF-α Immunoassay (R&D Systems), with Lipopolysaccharide (LPS, Wako) being used as a positive control for macrophage activation.

Figure 2:
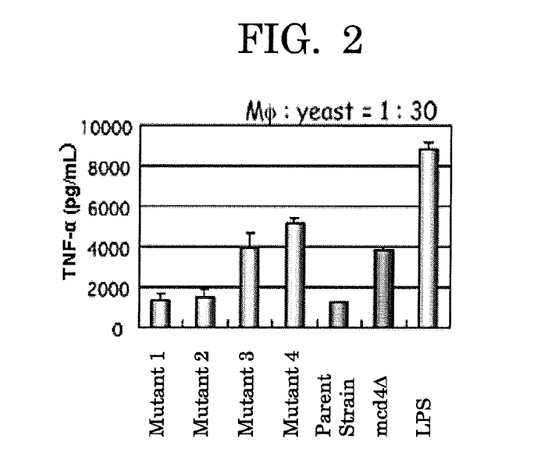
FIG. 2 is a bar graph showing the results of macrophage activation test of Mutants 1 to 4.

FIG. 2 shows the result of the macrophage activation capability test performed on Mutants 1 to 4. As shown in FIG. 2, Mutants 3 and 4 exhibited much stronger macrophage activation capability (immunopotentiating capability) compared to their parent strains.

Two strains (Mutants 3 and 4) out of the four strains (Mutants 1 to 4) were selected based on the results of the third screening.

Example 2

—Growth Test in Hypotonic Media—

The growth capability of Mutant 3 (obtained in Example 1) in a hypotonic medium was tested as follows.

Mutant 3 cells were pre-cultured in a uracil-containing YPDS liquid medium (1% by mass yeast extract (Oriental Yeast Co. Ltd.), 2% by mass peptone (Nihon Pharmaceutical Co. Ltd.), 2% by mass glucose (Kokusan Chemical Co. Ltd), 5.5% by mass (0.3 M) sorbitol (Wako Pure Chemical Industries Ltd.) and $6 \times 10^{-3}$% by mass uracil (Wako Pure Chemical Industries Ltd.), and the same manufacturers were used for the respective compounds throughout Examples). A uracil-containing YPD liquid medium and a uracil-containing YPDS liquid medium were inoculated with a part of the pre-culture so that $OD_{660}$ of each medium was adjusted to 0.1. The cultures were incubated at 30° C. with shaking, and a cell-count change over time (growth) of each culture was spectrophotoscopically evaluated on the basis of $OD_{660}$.

As control, the parent strain cells of Mutant 3 and the mutant cells produced using the technique disclosed in JP-A No. 2006-75039 (MCD4Δ) were also grown according to the same protocol as in Mutant 3, and a cell-count change over time (growth) for each strain were evaluated in the same manner.

Figure 3A:
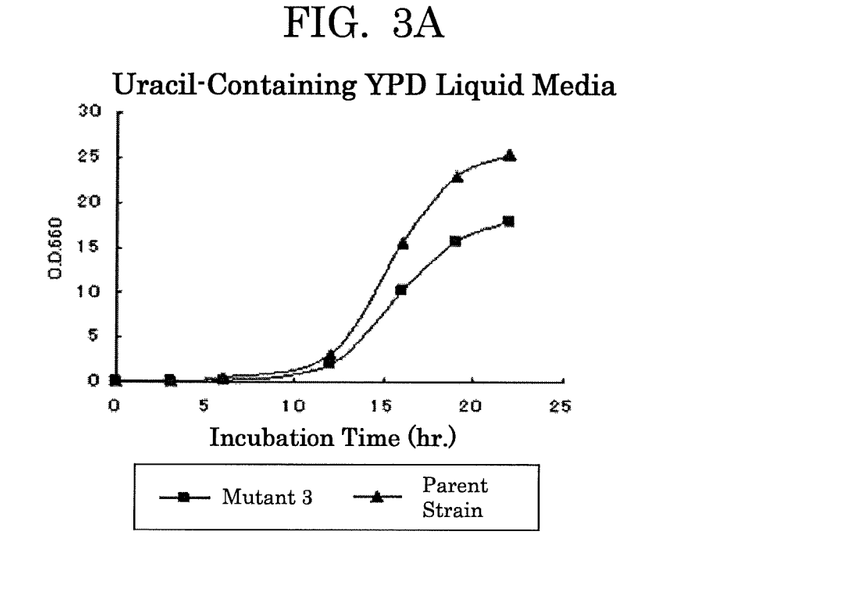
FIG. 3A is a line graph showing the results of the growth test of Mutant 3 and its parent strain.
Figure 3B:
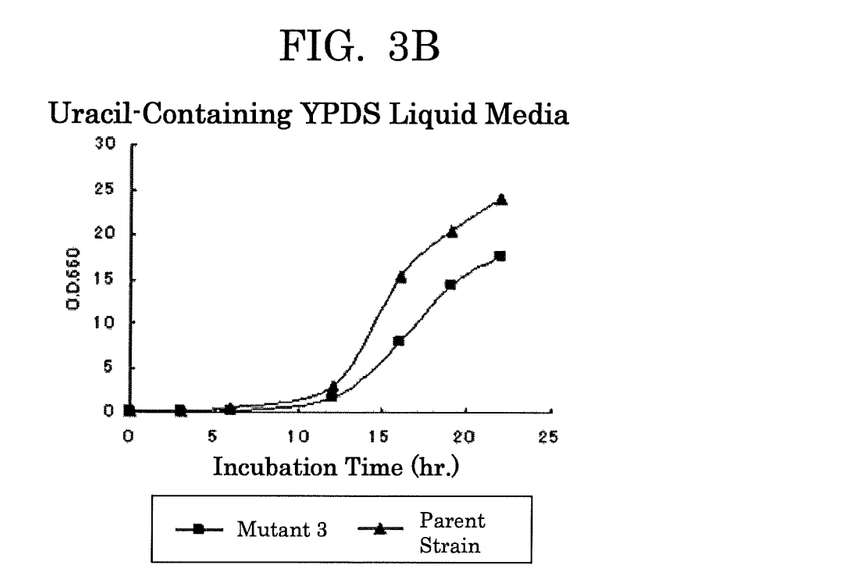
FIG. 3B is a line graph showing the results of the growth test of Mutant 3 and its parent strain.
Figure 4:
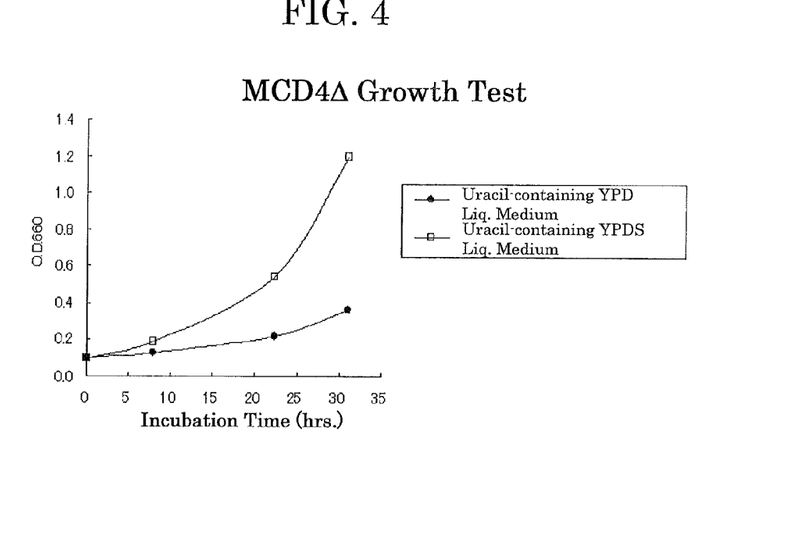
FIG. 4 is a line graph showing the results of the growth test of the mutant strain (MCD4Δ) described in JP-A No. 2006-75039.

FIGS. 3A and 3B show the results of the growth test of Mutant 3 and its parent strain. FIG. 4 shows the results of the growth test of the mutant disclosed in the JP-A No. 2006-75039 (MCD4Δ).

As shown in FIGS. 3A and 3B, the yeast of the present invention (Mutant 3) was able to grow in the hypotonic uracil-containing YPD liquid medium as well as in the uracil-containing YPDS medium with adjusted osmotic pressure, just like its parent strain did.

In contrast, as shown in FIG. 4, the mutant cells produced using the technique disclosed in JP-A No. 2006-75039 (MCD4Δ) grew very slowly in the hypotonic uracil-containing YPD liquid medium, although they grew relatively fast in the uracil-containing YPDS medium with adjusted osmotic pressure.

Example 3

—Manufacture of Compressed Live Yeast—

Compressed live yeast was manufactured from Mutant 3 obtained in Example 1.

Fed-batch culturing was performed using Mutant 3 cells (seed yeasts), which had been cultured in a uracil-containing YMPD liquid medium (0.3% by mass yeast extract, 0.3% by mass malt extract, 0.5% by mass peptone, 3% by mass glucose and $9 \times 10^{-3}$% by mass uracil). A sugar solution (sugar content (260 g/L), supplemented with urea (19.49 g/L) and $KH_2PO_4$ (52 g/L)) was continually added to the culture following a routinely used protocol. After completion of incubation, the culture broth was separated, washed with water, and filtered to obtain compressed live yeast.

Example 4

—Fermentability Test—

The compressed live yeast manufactured in Example 3 was used to test fermentability according to the method below.

The volume of gas generated for 120 minutes was measured according to the measurement method for yeast fermentability established by Japan Yeast Industry Association. The results are shown in Table 1.

TABLE 1

|  | Parent Strain | Mutant 3 |
| --- | --- | --- |
| Sugar-free Bread | 154 | 116 |
| White Bread | 171 | 142 |
| Sweet Pastry | 107 | 53 |
|  | mL $CO_2$/120 min. | |

As shown in Table 1, the fermentability of the yeast of the present invention (Mutant 3) was found to be relatively high, although it was less than that of the parent strain in numerical values. The mutant's fermentability exhibited in the manufacturing of both sugar-free and white bread was sufficient for practical use.

Example 5

—Manufacture of White Bread—

White bread was manufactured using the compressed live yeast of Example 3.

The white bread was manufactured using the ingredients shown in Table 2, through the following bread-making steps—the first rise, degassing, dividing, resting, shaping, proofing, and baking—while checking the extent of dough expansion.

TABLE 2

| Bread Manufacturing Test Ingredients | |
| --- | --- |
| Flour | 400 |
| Compressed Live Yeast | 8 |
| Salt | 8 |
| Sugar | 20 |
| Shortening | 16 |
| Water | 280 |
|  | (in g) |

Flavor characteristics, such as aroma and taste, as well as texture of the manufactured bread were comparable to those of conventional bread (manufactured using compressed live yeast of the parent yeast).

Example 6

—Manufacture of Dry Yeast Powder—

Dry yeast powder was manufactured using the compressed live yeast of Example 3.

The compressed live yeast was suspended in water, and the resultant suspension was spray-dried to loss on drying of less than 7% using a spray dryer (Ohkawara Kakohki Co. Ltd.). The settings used were as follows: hot gas temperature of 185° C., exhaust temperature of 100° C., and processing speed of 3 kg/hour.

Flavor characteristics, such as aroma and taste, as well as texture of the manufactured dry yeast powder were comparable to conventional dry yeast powder (manufactured using the parent strain).

Example 7

—Manufacture of Scone—

A scone was manufactured using the compressed live yeast of Example 3.

The compressed live yeast (4 g) obtained in Example 3 was added to 100 g of soft wheat flour, together with other ingredients, such as baking powder, sugar, salt, heavy cream, oil, and milk. The resultant dough was mixed and shaped at 24° C. The dough was left to stand for 30 minutes in a bread proofer set at 30° C./75% RH, and baked at 200° C. The scone was well fermented and had a peaked top (typical of scones made with conventional yeast).

Flavor characteristics, such as aroma and taste, as well as texture of the manufactured scone were comparable to the conventional scone (manufactured using the parent strain).

Example 8

—Manufacture of Dog Food—

Dog food was manufactured using the compressed live yeast obtained in Example 3.

The compressed live yeast obtained in Example 3 was added to the ingredients for the manufacturing of Laboratory Animal Feed DS-A (for dog) (Oriental Yeast Co. Ltd.) so that the dry content of the yeast in solid pellet would be 3%. The ingredients supplemented with the compressed live yeast was mixed, kneaded after addition of water, shaped into pellets, and dried. The normal manufacturing process of DS-A was successfully employed.

Example 9

—Macrophage Activation Capability Test—

The foods manufactured in Examples 6 and 7 were analyzed for macrophage activation capability according to the protocol described below.

RO water (80 g) was added to 20 g (in wet weight) of each food manufactured in Examples 6 and 7. The resultant mixture was mixed/homogenized using a homogenizer, to thereby obtain suspensions.

Macrophages were incubated for 2 days before use for the test. The macrophages were recovered from an incubation flask, washed twice in a new medium, and counted using a cell-counting chamber. The concentration of the macrophages was adjusted to a specified value, to thereby prepare a macrophage culture used in activity measurement.

The macrophage culture was dispensed into a 24-well plate ($2.5 \times 10^5$ cells/well). The food suspensions were added to each well so that the final food concentration was adjusted to the value indicated in FIG. 5. Then, the macrophage culture and the food suspensions were mixed with each other. After 6-hour incubation at 37° C. under 5% $CO_2$, the cultures were transferred to tubes, followed by centrifugation. The supernatant was recovered and the amount of TNF-α protein in the supernatant was analyzed using Quantikine Mouse TNF-α Immunoassay (R&D Systems), with Lipopolysaccharide (LPS, Wako) being used as a positive control for macrophage activation.

Figure 5:
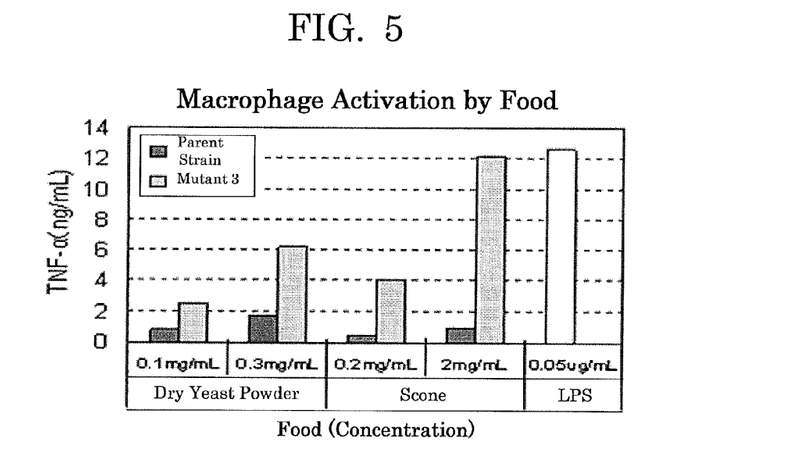
FIG. 5 is a bar graph showing the results of the macrophage activation test of a food containing Mutant 3, which is manufactured in Examples 6 and 7.

FIG. 5 shows the results of the macrophage activation capability of the foods containing Mutant 3 cells (manufactured in Examples 6 and 7).

As shown in FIG. 5, dry yeast powder and scone, manufactured using the yeast of the present invention (Mutant 3), exhibited macrophage activation capability increased depending on the amount of food added to the macrophage culture.

The yeast of the present invention possesses a superior immunopotentiating capability, and can be taken safely. Therefore, it may be suitably used to improve immune function of consumers, whose immune function has been compromised, as well as to prevent/treat diseases such as cancer, allergic symptoms, and infections. For instance, the yeast can be added to food raw materials or feeds. It may be used for manufacturing of food/beverages, such as fermentation of bread and beer.

What is claimed is:

1. Yeast comprising:
a cell wall including β-glucan and mannan at a low content of the mannan to an extent that the β-glucan is exposed on a surface of a cell of the yeast,
wherein the yeast has an immunopotentiating capability, and is capable of growing in an uracil-containing YPD liquid medium having osmotic pressure of 300 mOsm,
wherein, when a pre-culture of the yeast grown in an uracil-containing YPDS liquid medium is added to the uracil-containing YPD liquid medium so that $OD_{660}$ is adjusted to 0.1, followed by incubating at 30° C. for 24 hours, the yeast grows to increase the $OD_{660}$ of the uracil-containing YPD liquid medium to 1.0 or more,
the uracil-containing YPD liquid medium comprises 1% by mass of yeast extract, 2% by mass of peptone, 2% by mass of glucose, and $6 \times 10^{-3}$% by mass of uracil, and
the uracil-containing YPDS liquid medium comprises 1% by mass of yeast extract, 2% by mass of peptone, 2% by mass of glucose, 5.5% by mass (0.3 mol/L) of sorbitol, and $6 \times 10^{-3}$% by mass of uracil, and
wherein the yeast is in biologically pure culture,
the yeast is not recombinantly modified,
the yeast is mutated *Saccharomyces cerevisiae* and acquires the immunopotentiating capability through mutagenesis, which induces one or more mutations on chromosomes of *Saccharomyces cerevisiae*,
the chromosomes of the yeast have one or more mutations compared with the chromosomes of the *Saccharomyces cerevisiae* not going through the mutagenesis, and
the yeast is *Saccharomyces cerevisiae* FERM BP-11293 or *Saccharomyces cerevisiae* FERM BP-11294.

2. The yeast according to claim 1, wherein the immunopotentiating capability is a macrophage activating capability.

* * * * *